(12) United States Patent
Bae et al.

(10) Patent No.: US 11,978,007 B2
(45) Date of Patent: May 7, 2024

(54) SYSTEM, APPARATUS AND METHOD FOR COMPRESSING AND STORING DATA BASED ON THE AMOUNT OF CHANGE IN THE SENSED DATA USED FOR STATE MANAGEMENT OF LOGISTICS

(71) Applicant: Willog Co., Ltd., Seoul (KR)

(72) Inventors: Sung Hoon Bae, Seoul (KR); Ji Hyun Yun, Pyeongtaek-si (KR)

(73) Assignee: Willog Co., Ltd., Seoul (KR)

(*) Notice: Subject to any disclaimer, the term of this patent is extended or adjusted under 35 U.S.C. 154(b) by 237 days.

(21) Appl. No.: 17/570,430

(22) Filed: Jan. 7, 2022

(65) Prior Publication Data
US 2023/0153744 A1 May 18, 2023

(30) Foreign Application Priority Data
Nov. 15, 2021 (KR) .................. 10-2021-0156494

(51) Int. Cl.
*G06Q 10/0832* (2023.01)
*A61K 9/00* (2006.01)
*G06K 19/06* (2006.01)
*G06Q 10/087* (2023.01)

(52) U.S. Cl.
CPC ....... *G06Q 10/0832* (2013.01); *A61K 9/0019* (2013.01); *G06K 19/06037* (2013.01); *G06Q 10/087* (2013.01)

(58) Field of Classification Search
CPC .......... G06Q 10/0832; G06Q 10/087; A61K 9/0019; G06K 19/06037

USPC ......................................... 340/673
See application file for complete search history.

(56) References Cited

U.S. PATENT DOCUMENTS

| 2011/0074587 | A1* | 3/2011 | Hamm ................ G06Q 10/08 340/673 |
| 2015/0120597 | A1* | 4/2015 | Dertadian ............. F25D 3/08 705/332 |
| 2016/0260059 | A1* | 9/2016 | Benjamin ......... G06Q 10/0833 |
| 2017/0352002 | A1* | 12/2017 | Lam .................... G01V 15/00 |
| 2018/0218318 | A1* | 8/2018 | Passila ............. G06Q 10/083 |
| 2018/0300675 | A1* | 10/2018 | Arena ............... G07C 9/00182 |
| 2019/0049926 | A1* | 2/2019 | Beasley ............ G06K 19/0717 |
| 2019/0385115 | A1* | 12/2019 | Biermann ........... G01K 1/024 |

(Continued)

FOREIGN PATENT DOCUMENTS

KR 10-1872698 B1 6/2018

*Primary Examiner* — Kerri L Mcnally
(74) *Attorney, Agent, or Firm* — Studebaker & Brackett PC

(57) ABSTRACT

Disclosed is a storage method of sensed data used for state management of a logistics, which is performed by an apparatus including generating actual sensed data, which is obtained by sensing at least one of a temperature, acceleration, humidity, illuminance, inclination, impact, and location inside a region at a predetermined period through a first sensor installed inside the region where the logistics of a delivery vehicle is loaded, calculating a change amount of the actual sensed data at a predetermined time interval, activating one storage mode among a first storage mode and a second storage mode depending on a result of comparison between the change amount and a predetermined threshold change amount, and storing the actual sensed data in a storage method provided in the activated storage mode.

13 Claims, 11 Drawing Sheets

(56) References Cited

U.S. PATENT DOCUMENTS

2020/0311666 A1* 10/2020 Gray .................... G06K 7/1408
2021/0125143 A1* 4/2021 Bartlett .............. G06Q 10/0832

* cited by examiner

FIG. 8
| Pattern type | Pattern identifier | Pattern shape |
|---|---|---|
| First pattern | P1 | 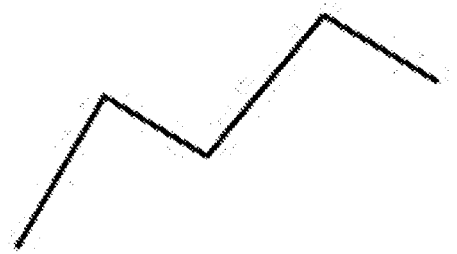 |
| Second pattern | P2 | 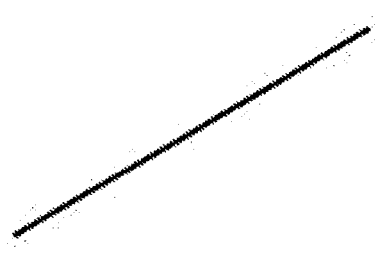 |
| Third pattern | P3 | 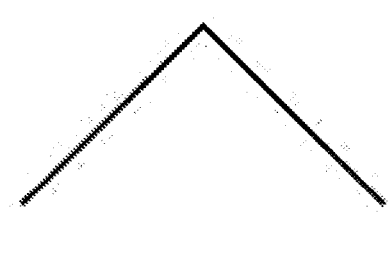 |
| ⋮ | P4 | ⋮ |
| N-th pattern | PN |  |

SYSTEM, APPARATUS AND METHOD FOR COMPRESSING AND STORING DATA BASED ON THE AMOUNT OF CHANGE IN THE SENSED DATA USED FOR STATE MANAGEMENT OF LOGISTICS

CROSS-REFERENCE TO RELATED APPLICATIONS

A claim for priority under 35 U.S.C. § 119 is made to Korean Patent Application No. 10-2021-0156494 filed on Nov. 15, 2021 in the Korean Intellectual Property Office, the entire contents of which are hereby incorporated by reference.

BACKGROUND

Embodiments of the inventive concept described herein relate to a system, apparatus and method for compressing and storing data based on the amount of change in sensed data used for state management of logistics.

Nowadays, as people buying things online increase and the development of the transportation industry makes long-distance transportation possible, the delivery volume of logistics is rapidly increasing. Besides, the delivery of vaccines has also become an important issue due to COVID-19.

In general, in a process of distribution, logistics are damaged due to temperature, humidity, and impact caused by properties of logistics, and thus it may be impossible to provide full quality logistics to customers.

Accordingly, it is necessary for a person who delivers logistics to directly identify status information such as the temperature, humidity, and impact of the inside of a delivery vehicle, to determine the state of the logistics, to prepare many paper certificates such as certificate documents or inspection papers including such the status information, and to provide the paper certificates to managers or customers.

However, because logistics shipments including vaccines are rapidly increasing, it is practically impossible for a person to understand and organize the logistics of the delivery vehicle one by one.

Accordingly, it is necessary to identify the status information of the logistics in the delivery vehicle that delivers the logistics, and to store and manage a large amount of the status information.

There is a prior art disclosed as Korean Patent Publication No. 10-1872698 (Patent Document 1).

SUMMARY

Embodiments of the inventive concept provide a method for storing status information of logistics, which is obtained by sensing at least one of the temperature, acceleration, humidity, illuminance, inclination, impact, and location of the inside of a delivery vehicle that delivers the logistics, in a predetermined storage method.

Problems to be solved by the inventive concept are not limited to the problems mentioned above, and other problems not mentioned will be clearly understood by those skilled in the art from the following description.

According to an embodiment, a storage method of sensed data used for state management of a logistics, which is performed by an apparatus includes generating actual sensed data, which is obtained by sensing at least one of a temperature, acceleration, humidity, illuminance, inclination, impact, and location inside a region at a predetermined period through a first sensor installed inside the region where the logistics of a delivery vehicle is loaded, calculating a change amount of the actual sensed data at a predetermined time interval, activating one storage mode among a first storage mode and a second storage mode depending on a result of comparison between the change amount and a predetermined threshold change amount, and storing the actual sensed data in a storage method provided in the activated storage mode.

Furthermore, the activating includes activating the first storage mode when the change amount is smaller than the threshold change amount.

Moreover, the first storage mode is a mode in which the actual sensed data is replaced with alternative sensed data including a pattern indicated by the change amount and is stored. The alternative sensed data is smaller in capacity than the actual sensed data. The second storage mode is a mode in which the actual sensed data is stored depending on an original capacity.

Also, the activating includes deactivating the first storage mode and activating the second storage mode while the first storage mode is activated, when the change amount is greater than the threshold change amount.

Besides, the method further includes storing, by the apparatus, pieces of identification information respectively indicating a plurality of patterns for each change amount, when the first storage mode is activated, identifying, by the apparatus, a pattern, which corresponds to the change amount, from among the plurality of patterns for each change amount, identifying, by the apparatus, identification information corresponding to the identified pattern from among the pieces of identification information, generating, by the apparatus, the alternative sensed data including the identified identification information, and storing, by the apparatus, the alternative sensed data instead of the actual sensed data.

In addition, the alternative sensed data further includes a time at which the actual sensed data is sensed.

Furthermore, the method further includes generating and displaying a two-dimensional code based on the alternative sensed data. The two-dimensional code is captured by an external terminal and is transmitted to a server.

Moreover, pieces of actual sensed data for each of the pieces of identification information are stored in a database of the server. The method further includes recognizing, by the server, the two-dimensional code within a capture image received from the terminal, recognizing, by the server, identification information within the recognized two-dimensional code, identifying, by the server, the recognized identification information among the pieces of identification information stored in the database, searching, by the server, for actual sensed data linked to the identified identification information, and managing, by the server, a state of the logistics based on the found result.

According to an embodiment, a storage apparatus of sensed data used for state management of a logistics includes a first sensor installed inside a region where the logistics of a delivery vehicle is loaded and sensing at least one of a temperature, acceleration, humidity, illuminance, inclination, impact, and location inside a region at a predetermined period and a processor that generates actual sensed data depending on the sensed result, calculates a change amount of the actual sensed data at a predetermined time interval, activates one storage mode among a first storage mode and a second storage mode depending on a result of comparison between the change amount and a predetermined threshold change amount, and stores the actual sensed data in a storage method provided in the activated storage mode.

In addition, another method, another apparatus, and another system for implementing the inventive concept, and a computer-readable recording medium for recording a computer program for performing the method may be further provided.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 8 is a diagram for describing a pattern according to the amount of change in actual sensed data, according to an embodiment of the inventive concept;

DETAILED DESCRIPTION

Figure 1:
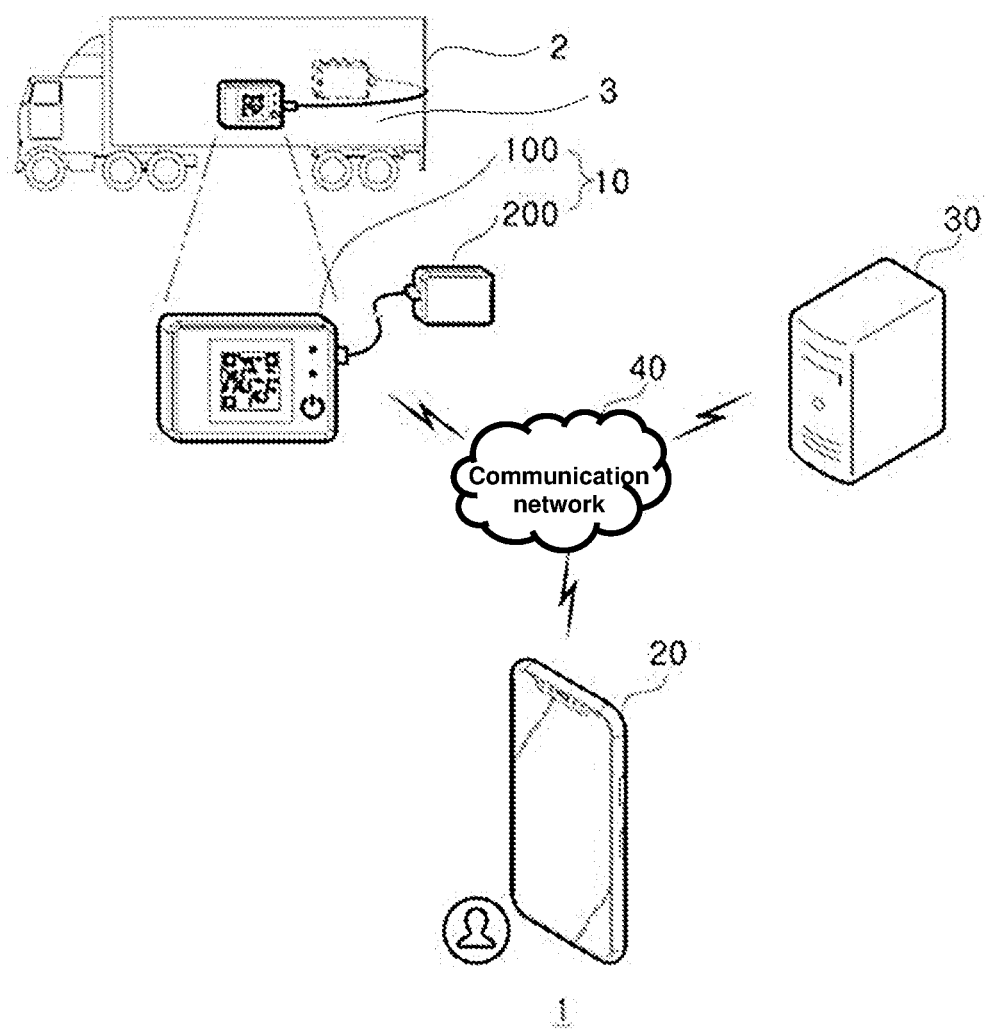
FIG. 1 is a diagram schematically illustrating a system for compressing and storing data based on the amount of change in sensed data used for state management of logistics, according to an embodiment of the inventive concept.

The above and other aspects, features and advantages of the inventive concept will become apparent from the following description of the following embodiments given in conjunction with the accompanying drawings. The inventive concept, however, may be embodied in various different forms, and should not be construed as being limited only to the illustrated embodiments. Rather, these embodiments are provided as examples so that the inventive concept will be thorough and complete, and will fully convey the scope of the inventive concept to those skilled in the art. The inventive concept may be defined by the scope of the claims.

The terms used herein are provided to describe embodiments, not intended to limit the inventive concept. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, activation described in the inventive concept may be a state where the power of a device [at least one of an apparatus 10 described below, a first sensor 200, and a second sensor 120, which are included in the apparatus 10] is turned on. Deactivation described in the inventive concept may be a state where the power of the device is turned off, or may be a state where a specific operation (e.g., a sensing operation) is paused in a turned-on state. In this case, when the device is activated again in a deactivated state, a specific operation may be resumed.

Hereinafter, an embodiment of the inventive concept will be described in detail with reference to the accompanying drawings.

FIG. 1 is a diagram schematically illustrating a system 1 for compressing and storing data based on the amount of change in sensed data used for state management of logistics, according to an embodiment of the inventive concept.

Figure 2:
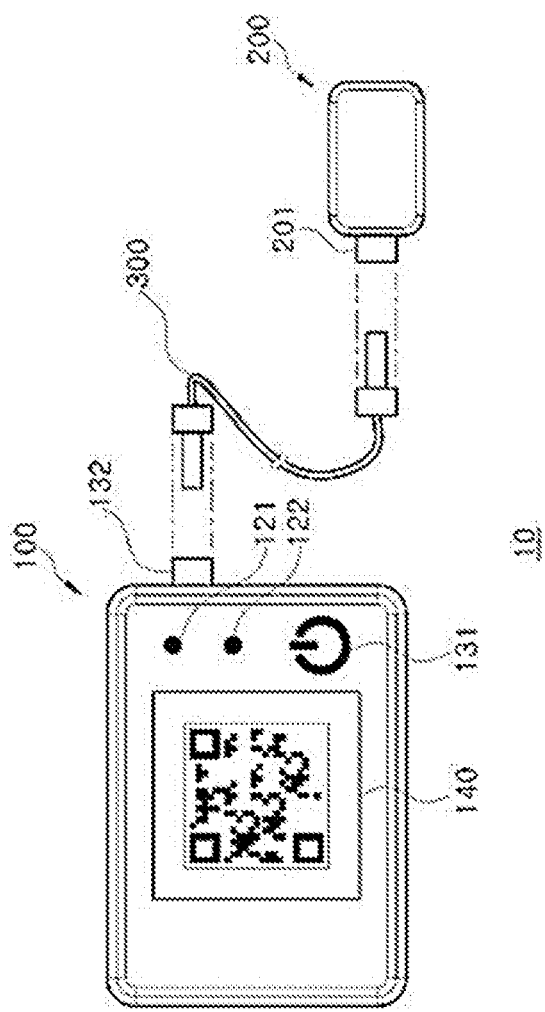
FIGS. 2 to 3 are diagrams for describing an apparatus for compressing and storing data based on the amount of change in sensed data used for state management of logistics, according to an embodiment of the inventive concept.
Figure 3:
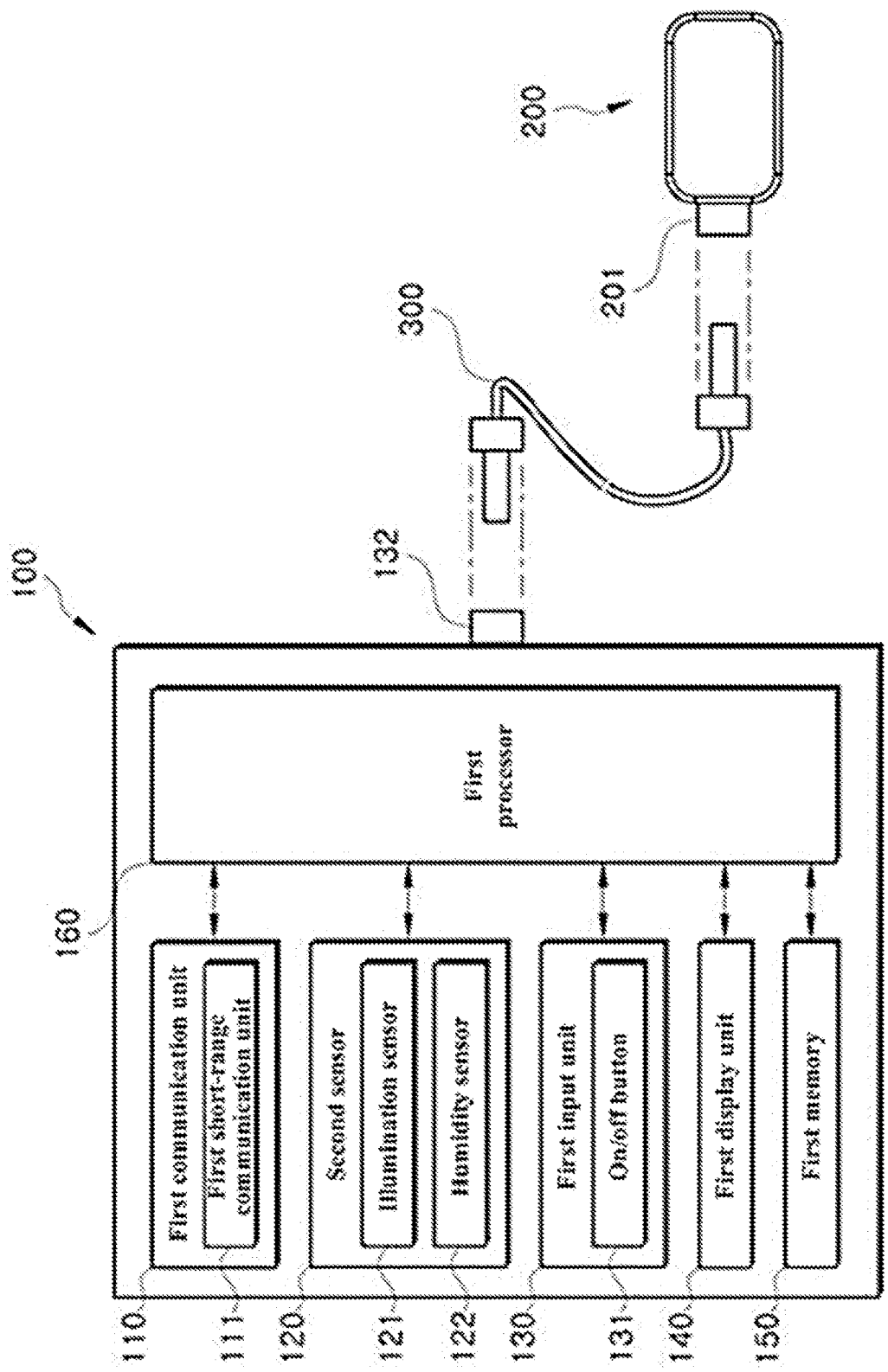

FIGS. 2 to 3 are diagrams for describing an apparatus 10 for compressing and storing data based on the amount of change in sensed data used for state management of logistics, according to an embodiment of the inventive concept.

Figure 4:
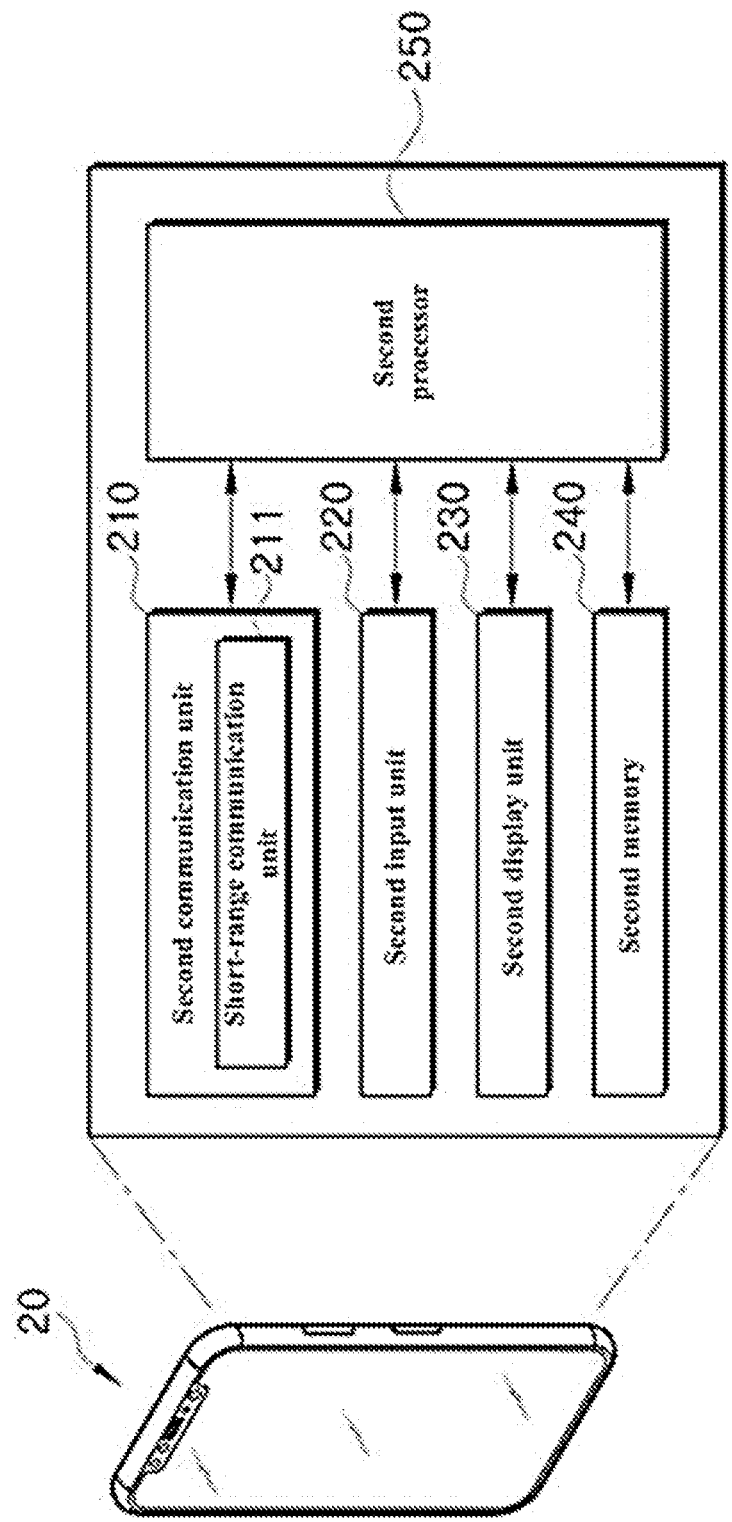
FIG. 4 is a diagram for describing an external terminal, according to an embodiment of the inventive concept.

FIG. 4 is a diagram for describing an external terminal 20, according to an embodiment of the inventive concept.

Figure 5:
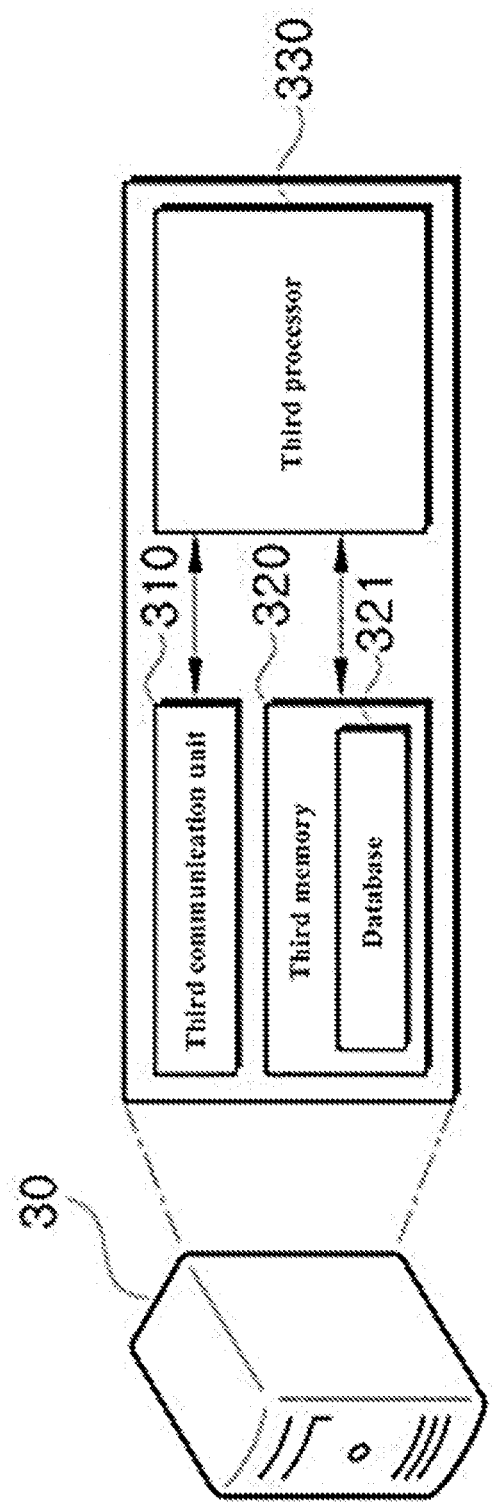
FIG. 5 is a diagram for describing a server, according to an embodiment of the inventive concept.

FIG. 5 is a diagram for describing a server 30, according to an embodiment of the inventive concept.

Figure 6:
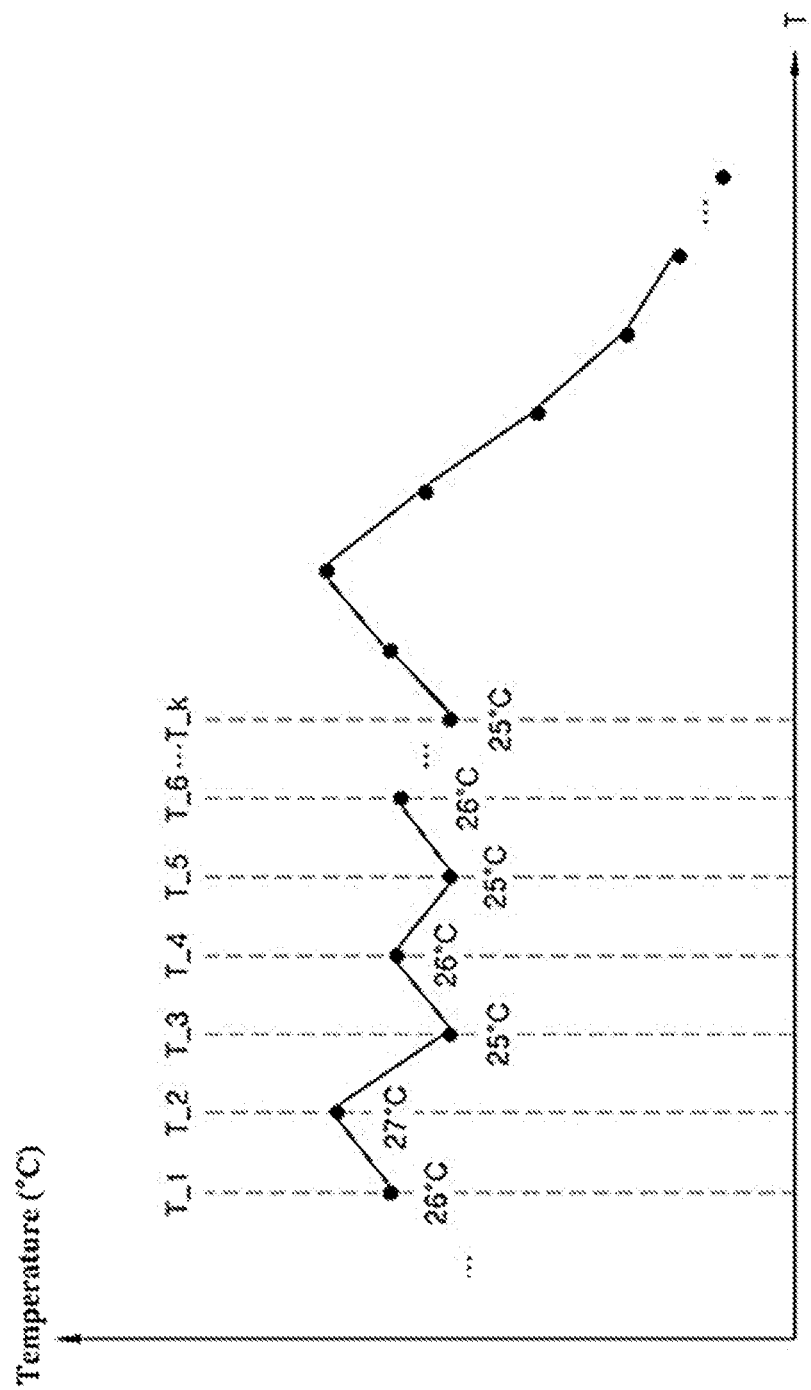
FIGS. 6 to 7 are diagrams for describing actual sensed data for temperature, according to an embodiment of the inventive concept.
Figure 7:
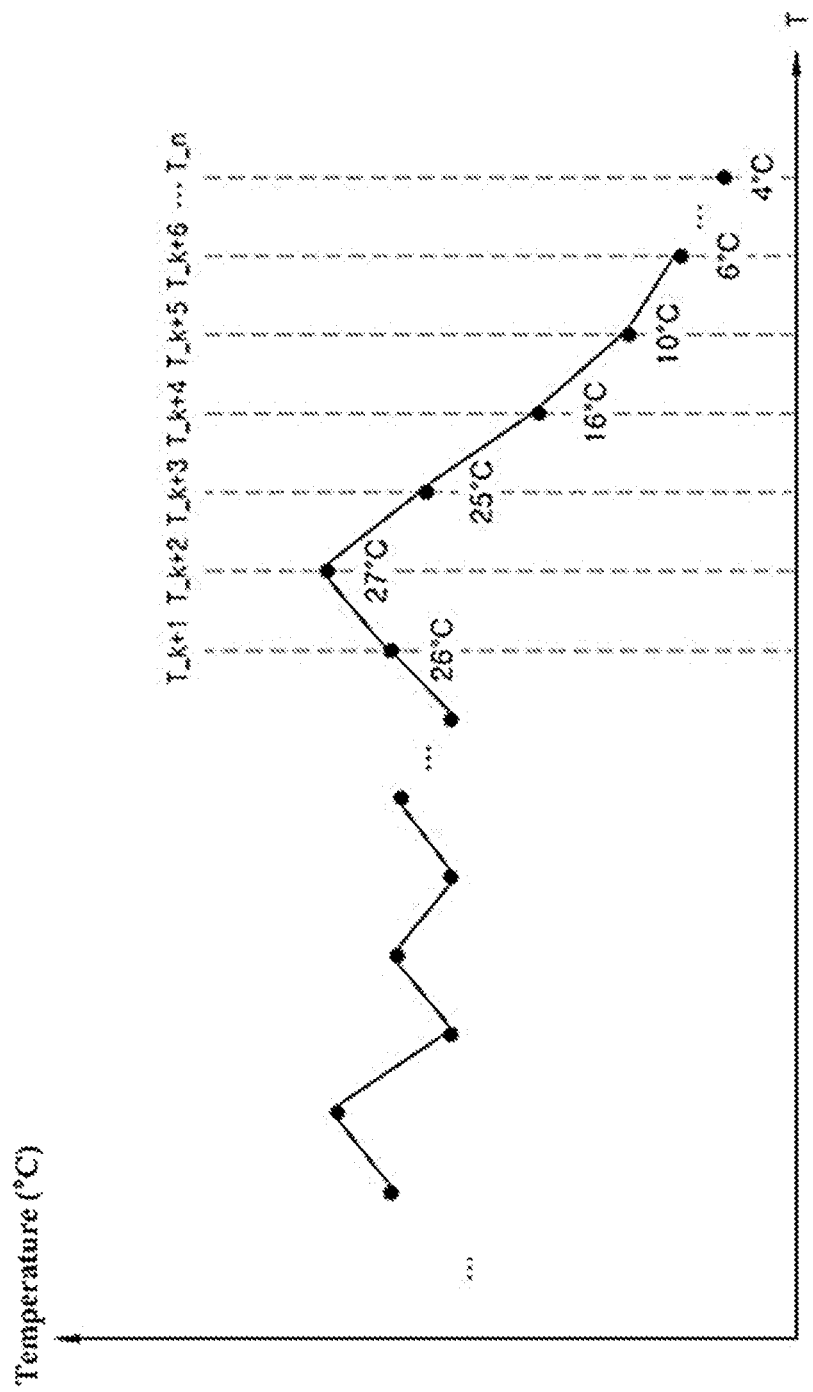

FIGS. 6 to 7 are diagrams for describing actual sensed data for temperature, according to an embodiment of the inventive concept.

FIG. 8 is a diagram for describing a pattern according to the amount of change in actual sensed data, according to an embodiment of the inventive concept.

Figure 9:
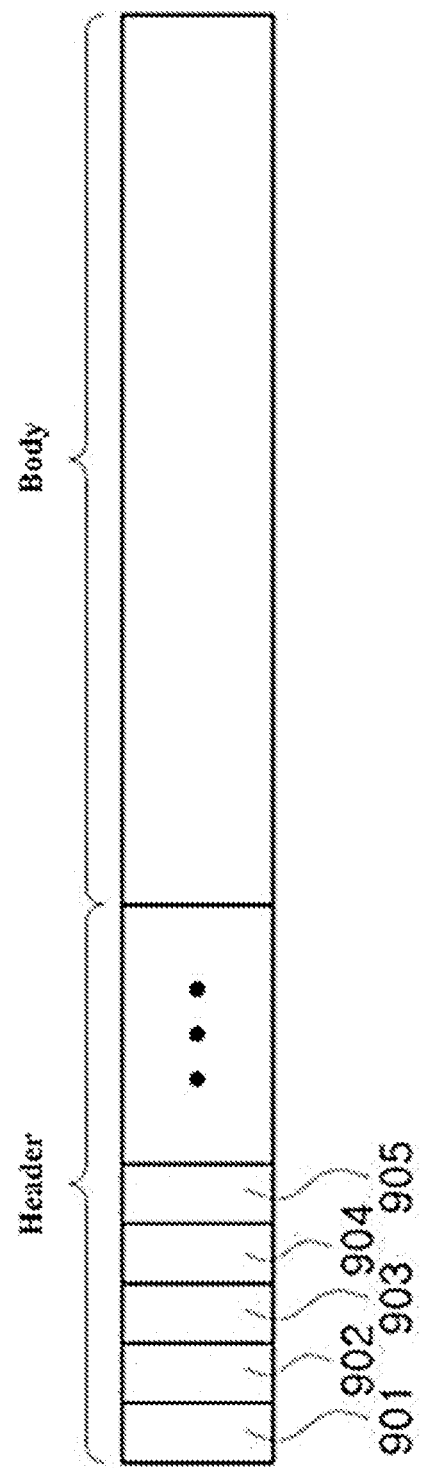
FIG. 9 is a diagram for describing a data structure of alternative sensed data or actual sensed data, according to an embodiment of the inventive concept.

FIG. 9 is a diagram for describing a data structure of alternative sensed data or actual sensed data, according to an embodiment of the inventive concept.

Hereinafter, the system 1 for compressing and storing data based on the amount of change in sensed data used for state management of logistics according to an embodiment of the inventive concept will be described with reference to FIGS. 1 to 9. Herein, the system 1 may include fewer or more components than the components illustrated in FIG. 1.

The system 1 may include an apparatus 10 that measures the state of a logistics, a terminal 20 that recognizes a two-dimensional code provided by the apparatus 10, a server 30 that manages the state of the logistics by grasping sensed data indicated by the two-dimensional code through the decoding of the two-dimensional code received from the terminal 20, a communication network 40, and an external server (not shown).

First of all, the apparatus 10 will be described with reference to FIGS. 2 and 3. The apparatus 10 may be provided in the shape shown in FIG. 2.

The apparatus 10 may generate actual sensed data obtained by periodically sensing at least one of the temperature, acceleration, humidity, illuminance, inclination, impact, and location inside a region through the first sensor 200 installed inside a region 3 where the logistics of a delivery vehicle 2 is loaded.

Here, the apparatus 10 may calculate the amount of change in actual sensed data at the predetermined time interval, and then may activate one storage mode among the first storage mode and the second storage mode depending on the result of comparison between the change amount and a predetermined threshold change amount.

Moreover, the apparatus 10 may store the actual sensed data in a storage method provided by the activated storage mode.

Accordingly, the apparatus 10 may store and manage the capacity of data indicating status information of a logistics by providing a method for storing status information of logistics, which is obtained by sensing at least one of the temperature, acceleration, humidity, illuminance, inclination, impact, and location of the inside of a delivery vehicle that delivers the logistics, in a predetermined storage method.

Moreover, the apparatus 10 may store a lot of data in one page by compressing the status information stored in a form of a two-dimensional code (e.g., a QR code or a barcode), thereby increasing the efficiency of logistics-related task.

Here, the apparatus 10 is detachable. Accordingly, when the delivery vehicle 2 is scrapped or re-purposed while the apparatus 10 is attached to the region 3 where the logistics of the delivery vehicle 2 are loaded, the apparatus 10 may be collected from the region 3 and then may be recycled. Here, the region 3 where the logistics of the delivery vehicle 2 is loaded may be a container box provided integrally with the delivery vehicle 2 or may be in a form of a detachable container box.

Referring to FIG. 1, the apparatus 10 is shown as one apparatus installed in the region 3 where the logistics of the single delivery vehicle 2 is loaded, but is not necessarily limited thereto. For example, the plurality of apparatuses 10 may be installed in the region 3, and may be installed in a detachable form anywhere in the region 3.

The apparatus 10 may include a body 100 and a first sensor 200. In detail, the body 100 of the apparatus 10 may be detachably attached to the outside of the region 3 where the logistics of the delivery vehicle 2 are loaded. The first sensor 200 of the apparatus 10 may be detachably attached to the inside of the region 3 where the logistics of the delivery vehicle 2 are loaded.

First of all, the at least one first sensor 200 of the apparatus 10 may be installed inside the region 3 so as to sense at least one of the temperature, acceleration, humidity, illuminance, inclination, impact, and location inside the region 3.

Here, the body 100 may control the driving or operation of the first sensor 200 of the apparatus 10 based on sensed data or may perform data processing, function, or operation associated with an application program installed in the body 100.

For example, the first sensor 200 may include at least one or two or more of an illumination sensor, a humidity sensor, a proximity sensor, an acceleration sensor, a G-sensor, a gyroscope sensor, a motion sensor, an infrared (IR) sensor, a finger scan sensor, an optical sensor, an ultrasonic sensor, an infrared ray sensor, an environmental sensor (e.g., a barometric pressure sensor, a temperature sensor, a radiation detection sensor, a heat detection sensor, a gas detection sensor, or the like), a chemical sensor (e.g., a healthcare sensor, a biometric sensor, or the like), a location sensor, an ethylene sensor, a $CO_2$ sensor and a nitrogen sensor.

Here, the proximity sensor refers to a sensor that detects whether there is an object approaching a predetermined detection surface or an object existing in the vicinity, without mechanical contact by using the power of an electromagnetic field or infrared light.

At least one of these sensors may be embedded in the first sensor 200.

Furthermore, the first sensor 200 may include a second AUX terminal 201 for connecting to a first AUX terminal 132 of the body 100 through an AUX cable 300. Here, the first sensor 200 may be activated only when the first sensor 200 is connected to the first AUX terminal 132 of the body 100 through the AUX cable 300.

Moreover, the first sensor 200 may have a sensitivity level range different from that of the second sensor 120.

Besides, the first sensor 200 may have a sensitivity level range optimized to manage the logistics.

For example, when the logistics is a vaccine, the first sensor 200 may have a sensitivity level range optimized depending on the type of a vaccine.

That is, when the logistics is a vaccine made by Pfizer among vaccines, because a temperature range to be maintained during delivery is −90 to −60° C., the apparatus 10 may be provided with the first sensor 200 capable of measuring the temperature range.

Alternatively, when the logistics is a vaccine made by Moderna among vaccines, because a temperature range to be maintained during delivery is −20° C., the apparatus 10 may be provided with the first sensor 200 capable of measuring the temperature range.

Accordingly, the first sensor 200 may have a sensitivity level range that is different depending on the type of a logistics. When the sensitivity level range is changed depending on the type of a logistics, the first sensor 200 may also be replaced and then attached to the region 3.

Next, the body 100 of the apparatus 10 may include a first communication unit 110, a second sensor 120, a first input unit 130, a first display unit 140, a first memory 150, and a first processor 160. Such the apparatus 10 may include fewer or more components than the components illustrated in FIGS. 2 and 3.

The first communication unit 110 may include one or more modules that enable wireless communication between the apparatus 10 and a wireless communication system, between the apparatus 10 and the external terminal 20, between the apparatus 10 and a server 30, or between the apparatus 10 and an external server (not illustrated). Furthermore, the first communication unit 110 may include one or more modules connecting the apparatus 10 to one or more networks.

Moreover, the first communication unit 110 may be a module for obtaining a location (or a current location) of the apparatus 10 and may typically include a global positioning system (GPS) module or a Wireless Fidelity (Wi-Fi) module.

For example, the body 100 of the apparatus 100 may obtain the location through a signal received from a GPS satellite through the GPS module. As another example, when the body 100 of the apparatus 100 utilizes the Wi-Fi module, the body 100 of the apparatus 100 may obtain the location based on information of a wireless access point (AP) that transmits or receives wireless signals to or from the Wi-Fi module. The first communication unit 110 is not limited to directly calculating or obtaining the location of the body 100 of the apparatus 100.

Moreover, the first communication unit 110 may further include a first short-range communication unit 111 that performs low-power Bluetooth (Bluetooth™ Low Energy) communication with the external terminal 20.

The second sensor 120 may sense at least one of the temperature, acceleration, humidity, illuminance, inclination, impact, location, and proximity of the outside of the region 3 where the logistics of the delivery vehicle 2 are loaded.

Here, on the basis of the sensed data, the first processor 160 may control the driving or operation of the body 100 or may perform data the processing, function, or operation associated with an application program installed in the apparatus 10.

For example, the second sensor 120 may include at least one or two or more of an illumination sensor 121, a humidity sensor 122, a proximity sensor, an acceleration sensor, a G-sensor, a gyroscope sensor, a motion sensor, an infrared (IR) sensor, a finger scan sensor, an optical sensor, an ultrasonic sensor, an infrared ray sensor, an environmental sensor (e.g., a barometric pressure sensor, a temperature sensor, a radiation detection sensor, a heat detection sensor, a gas detection sensor, or the like), a chemical sensor (e.g., a healthcare sensor, a biometric sensor, or the like), a location sensor, an ethylene sensor, a $CO_2$ sensor and a nitrogen sensor.

Here, the proximity sensor refers to a sensor that detects whether there is an object approaching a predetermined detection surface or an object existing in the vicinity, without mechanical contact by using the power of an electromagnetic field or infrared light.

The illumination sensor 121 and the humidity sensor 122 may be provided on one surface of the body 100. In addition, the remaining sensors may be provided inside the body 100.

Here, on the basis of the sensed signal according to the sensed result of the above-described one or more sensors, the first processor 160 may control the driving or operation of the body 100 of the apparatus 10 or may perform the data processing, function, or operation associated with an application program installed in the apparatus 10. Accordingly, the first processor 160 may combine and utilize pieces of information sensed by at least two or more of these sensors.

The second sensor 120 may be deactivated only when the first AUX terminal 132 of the body 100 is connected to the first sensor 200 through the AUX cable 300.

Moreover, the second sensor 120 may have a sensitivity level range different from that of the first sensor 200.

The first input unit 130 may be used to enter image information (or signal), audio information (or signal), data, or information entered by a user. The first input unit 130 may include an on/off button 131 and the first AUX terminal 132.

Also, the body 100 of the apparatus 10 may include at least one first camera (not shown) such that the first input unit 130 enters image information. The first camera (not illustrated) may process an image frame such as a still image or a moving image, which is obtained by an image sensor in a shooting mode. The processed image frame may be displayed on the first display unit 140 or may be stored in the first memory 150. Also, the first camera (not illustrated) may include at least one of a camera for recognizing an iris and a camera for capturing an image.

Besides, the first input unit 130 further includes at least one button among a time setting button (not shown) for starting the apparatus 10 or controlling the screen of the first display unit 140, and an adjustment button (not shown) for displaying a QR code.

Here, the button may be implemented with a physical hardware button or a virtual button displayed on a touch screen. For the virtual button, the virtual button may be generated on the first display unit 140 in a form of the touch screen.

Furthermore, the on/off button 131 may be formed as a physical button, a touch pad-type touch button, or a virtual button displayed on a touch screen.

Accordingly, when the on/off button 131 is maintained as being pressed during a predetermined first time (hereinafter referred to as a "long key input"), the apparatus 10 may be turned on or off.

Moreover, the apparatus 10 may be initialized when the input of a long key is entered into the on/off button 131 during a predetermined second time. Here, the initialization may be a function in which all QR codes pre-stored in the apparatus 10 are deleted (in this case, a pre-stored QR code may be deleted after the QR code is transmitted to a predetermined external device), may be a function in which the unit count is set as a default (factory reset) count, and may be a function in which the operation mode of the apparatus 10 is set as a default (factory initialization) mode. In addition, the first time (e.g., '5 seconds') may mean a shorter time than the second time (e.g., '6 seconds or more').

Moreover, when the on/off button 131 is input while the illuminance value measured from the illumination sensor 121 is not greater than a predetermined illuminance value, the apparatus 10 may change a unit count for generating a QR code depending on an input method of the on/off button 131.

For example, while a user covers the illumination sensor 122 with his/her finger, the unit count may be changed into 1 minute depending on one-time input of the on/off button 131, and the unit count may be changed into 3 minute depending on two-time input of the on/off button 131. That is, the unit count may be changed into 1 minute, 3 minutes, 30 minutes, 1 hour, 2 hours, 6 hours, or the like based on the number of times that the on/off button 131 is entered by the user.

Besides, the first AUX terminal 132 may be provided for connection with the first sensor 200 through the AUX cable 300.

The first display unit 140 may have a mutual layer structure with the touch sensor or may be integrally formed with the touch sensor, and thus a touch screen may be implemented. Such the touch screen may provide an input interface between the apparatus 10 and a user and may, at the same time, provide an output interface between the apparatus 10 and the user. The first display unit 140 may display a QR provided by the apparatus 10.

The first memory 150 may store data for supporting various functions of the apparatus 10, especially a QR code. The first memory 150 may store a plurality of application programs (or applications) running in the apparatus 10, data for an operation of the apparatus 10, and instructions. At least part of the application programs may be downloaded from an external server (not illustrated) through wireless communication. Besides, at least part of the application programs may be present for basic functions of the apparatus 10. In the meantime, the application program may be stored in the first memory 150, may be installed in the apparatus 10, and may be driven by the first processor 160 so as to perform an operation (or function) of the apparatus 10.

Here, the first memory 150 may store piece of identification information respectively indicating a plurality of patterns for each change amount.

In addition to an operation associated with the application program, the first processor 160 may generally control overall operations of the apparatus 10. The first processor 160 may provide or process appropriate information or functions to a user, by processing a signal, data, information, or the like, which is input or output through the above-described components, or driving the application program stored in the first memory 150.

Besides, the first processor 160 may control at least part of the components described with reference to FIGS. 2 and 3 to operate the application program stored in the first memory 150. Furthermore, the first processor 160 may combine and operate at least two or more of the components included in the apparatus 10 to operate the application program.

The first processor 160 may generate actual sensed data obtained by periodically sensing at least one of the temperature, acceleration, humidity, illuminance, inclination, impact and location inside the region 3 through the first sensor 200 installed in the region 3 where the logistics of the delivery vehicle 2 is loaded.

Here, the actual sensed data may be generated with respect to one of the temperature, acceleration, humidity, illuminance, inclination, impact, and location, or may be generated with respect to a combination of two or more.

Moreover, the first processor 160 may calculate a change amount of the actual sensed data at a predetermined time interval.

Here, the predetermined time interval may include a first time interval to an N-th time interval. As a time goes from the first time interval to the N-th time interval, the length of the time interval may be set to be longer.

In addition, the predetermined time interval may be set depending on the type of a logistics loaded in the delivery vehicle 2. For example, when the type of a logistics is a vaccine, because the vaccine is sensitive to a temperature change, the first processor 160 may generate actual sensed data for temperature by setting a time interval so as to be shorter.

Referring to FIGS. 6 and 7, for example, the first processor 160 may generate actual sensed data for the temperature, which is obtained by sensing a temperature of the region 3 where the logistics of the delivery vehicle 2 is loaded, through the first sensor 200 at each predetermined period T.

Hereinafter, 'k' and 'n' described with reference to FIGS. 6 to 7 may be integers, and 'k' may be less than 'n'.

Here, the temperature sensed in T_1 may be 26 degrees; the temperature sensed in T_2 may be 27 degrees; the temperature sensed by T_3 may be 25 degrees; the temperature sensed by T_4 may be 26 degrees; the temperature sensed by T_5 may be 25 degrees; the temperature sensed by T_6 may be 26 degrees; and, the temperature sensed in T_k may be 25 degrees.

For example, the first processor 160 may convert the sensed temperature at each predetermined period into hexadecimal, may allocate 2 bytes to a hexadecimal number, and may store the converted result in the first memory 150.

Here, the temperature of 26 degrees sensed at T_1 may be converted to a hexadecimal number of 0x1A; the temperature of 27 degrees sensed at T_2 may be converted to a hexadecimal number of 0x1B; the temperature of 25 degrees sensed at T_3 may be converted to a hexadecimal number of 0x19; the temperature of 26 degrees sensed at T_4 may be converted to a hexadecimal number of 0x1A; the temperature of 25 degrees sensed at T_5 may be converted to a hexadecimal number of 0x19; the temperature of 26 degrees sensed at T_6 may be converted to a hexadecimal number of 0x1A; and, the temperature of 25 degrees sensed at T_k may be converted to a hexadecimal number of 0x19.

Afterward, the first processor 160 may calculate a change amount D_k of the actual sensed data for the temperature at the predetermined time interval.

Here, the predetermined time interval may be variously set to morning or afternoon, 6 hours, 4 hours, or the like. In FIG. 6, the predetermined time interval may include T_1 to T_k.

That is, with respect to the predetermned time interval of T_1 to T_k, the first processor 160 may calculate a first change amount D_1 of +1 between the temperature of 26 degrees sensed at T_1, and the temperature of 27 degrees sensed at T_2; the first processor 160 may calculate a second change amount D_2 of −2 between the temperature of 27 degrees sensed at T_2, and the temperature of 25 degrees sensed at T_3; the first processor 160 may calculate a third change amount D_3 of +1 between the temperature of 25 degrees sensed at T_3, and the temperature of 26 degrees sensed at T_4; the first processor 160 may calculate a fourth change amount D_4 of −1 between the temperature of 26 degrees sensed at T_4, and the temperature of 25 degrees sensed at T_5; the first processor 160 may calculate a fifth change amount D_5 of +1 between the temperature of 25 degrees sensed at T_5, and the temperature of 26 degrees sensed at T_6; and, the first processor 160 may calculate a change amount "D_k−1 (=T_k−T_k−1)" between the temperature sensed at T_k−1, and the temperature of sensed at T_k.

Referring to FIG. 7, the first processor 160 may generate actual sensed data for the temperature, which is obtained by sensing a temperature of the region 3 where the logistics of the delivery vehicle 2 is loaded, through the first sensor 200 at each predetermined period T.

Here, the temperature sensed at T_k+1 may be 26 degrees; the temperature sensed at T_k+2 may be 27 degrees; the temperature sensed at T_k+3 may be 25 degrees; the temperature sensed at T_k+4 may be 16 degrees; the temperature sensed at T_k+5 may be 10 degrees; the temperature sensed at T_k+6 may be 6 degrees; and, the temperature sensed at T_n may be 4 degrees.

For example, the first processor 160 may convert the sensed temperature at each predetermined period into hexadecimal, may allocate 2 bytes to a hexadecimal number, and may store the converted result in the first memory 150.

Here, the temperature of 26 degrees sensed at T_k+1 may be converted to a hexadecimal number of 0x1A; the temperature of 27 degrees sensed at T_k+2 may be converted to a hexadecimal number of 0x1B; the temperature of 25 degrees sensed at T_k+3 may be converted to a hexadecimal number of 0x19; the temperature of 16 degrees sensed at T_k+4 may be converted to a hexadecimal number of 0x10; the temperature of 10 degrees sensed at T_k+5 may be converted to a hexadecimal number of 0x0A; the temperature of 6 degrees sensed at T_k+6 may be converted to a hexadecimal number of 0x06; and, the temperature of 4 degrees sensed at T_n may be converted to a hexadecimal number of 0x04.

Afterward, the first processor 160 may calculate a change amount D_n of the actual sensed data for the temperature at the predetermined time interval.

Here, the predetermined time interval may be variously set to morning or afternoon, 6 hours, 4 hours, or the like. In FIG. 7, the predetermined time interval may include T_k+1 to T_n.

That is, with respect to the predetermined time interval of T_k+1 to T_n, the first processor 160 may calculate a (k+1)-th change amount D_k+1 of +1 between the temperature of 26 degrees sensed at T_k+1, and the temperature of 27 degrees sensed at T_k+2; the first processor 160 may calculate a (k+2)-th change amount D_k+2 of −2 between the temperature of 27 degrees sensed at T_k+2, and the temperature of 25 degrees sensed at T_k+3; the first processor 160 may calculate a (k+3)-th change amount D_k+3 of −9 between the temperature of 25 degrees sensed at T_k+3, and the temperature of 16 degrees sensed at T_k+4; the first processor 160 may calculate a (k+4)-th change amount D_k+4 of −6 between the temperature of 16 degrees sensed at T_k+4, and the temperature of 10 degrees sensed at T_k+5; the first processor 160 may calculate a (k+5)-th change amount D_k+5 of −4 between the temperature of 10 degrees sensed at T_k+5, and the temperature of 6 degrees sensed at T_k+6; and, the first processor 160 may calculate a change amount D_n−1(=T_n−T_n−1) between the temperature sensed at T_n−1, and the temperature sensed at T_n.

The first processor 160 may activate one storage mode among the first storage mode and the second storage mode depending on the result of comparison between the change amount and a predetermined threshold change amount.

In detail, when the change amount is less than the threshold change amount, the first processor 160 may activate the first storage mode. When the change amount is greater than the threshold change amount, the first processor 160 may activate the second storage mode.

For example, the first processor 160 may compare the change amount of +1, −2, +1, −1, or 1 with a threshold change amount having a range of −8 to 7, or −7 to 8. When the change amount is small, the first processor 160 may activate the first storage mode.

That is, the first processor 160 may compare the change amount with the threshold change amount having a range of −8 to 7. When the change amount is smaller than the threshold change amount, the first processor 160 may activate the first storage mode.

As another example, the first processor 160 may compare the change amount of +1, −2, −9, −6, or −3 with a threshold change amount having a range of −8 to 7, or −7 to 8. Because a change amount of +1, −2, −6, or −3 is small, but a change amount of −9 is great, the first processor 160 may activate the second storage mode.

That is, the first processor 160 may compare the change amount with the threshold change amount having a range of −8 to 7. When the change amount is greater than the threshold change amount, the first processor 160 may activate the second storage mode.

Here, the threshold change amount may be −8 to 7, and may be 0111: 7, 0110: 6, 0101:5, 0100: 4, 0011:3, 0010: 2, 0001: 1, 0000: 0, 1111: −1 (complement), 1110: −2 (complement), . . . , 1001: −7 (complement), or 1000: −8 (complement).

First of all, the first storage mode may be a mode in which the actual sensed data is replaced with alternative sensed data including a pattern indicated by the change amount and then stored.

Here, the alternative sensed data may have a smaller capacity than the actual sensed data and may further include a time at which the actual sensed data is sensed.

For example, referring to FIG. 8, a plurality of patterns for each change amount may include a first pattern, a second pattern, a third pattern to an N-th pattern. Identification information indicating the first pattern may be P1; identification information indicating the second pattern may be P2; identification information indicating the third pattern may be P3; and, identification information indicating the N-th pattern may be a PN.

Here, the plurality of patterns for each change amount may include a pattern in which the actual sensed data is maintained within a specific range in the corresponding time interval, or which is changed with regularity.

Moreover, the plurality of patterns for each change amount may be patterned based on values previously sensed at the same location (GPS information) and in the same time zone. The pattern for each of the plurality of change amount may be generated in a form of a table by assigning pattern identification information to each pattern for each of the plurality of change amount, and may be stored in the first memory 150 of the apparatus 10 in a firmware method.

For example, the plurality of patterns for each change amount may be generated based on factors such as the highest value of a change amount, the lowest value of the change amount, and the period of a waveform depending on the change amount calculated based on the previously sensed actual sensed data.

When the first storage mode is activated, the first processor 160 may identify a pattern corresponding to the change amount from among the plurality of patterns for each change amount stored in the first memory 150.

That is, the first memory 150 may store a table in which the corresponding identification information about a pattern indicating each of the plurality of change amounts is mapped onto the corresponding actual sensed data.

Moreover, the first processor 160 may identify identification information corresponding to the identified pattern among the pieces of identification information.

Moreover, the first processor 160 may store the actual sensed data in a storage method provided by the activated storage mode.

In detail, the first processor 160 may generate the alternative sensed data including the identified identification information based on the storage method provided by the activated first storage mode and then may store the alternative sensed data instead of the actual sensed data.

That is, the first processor 160 may search for a pattern corresponding to the change amount of the actual sensed data within the currently sensed interval in the table and then may replace and store alternative sensed data including identification information mapped onto the found pattern instead of storing the actual sensed data.

Here, for example, when the actual sensed data is stored in the storage method provided in the first storage mode, a bitstream included in a data structure is as follows.

First of all, a first bitstream BITSTREAM1 generated based on the change amount of the actual sensed data is as follows.

BITSTREAM1: {(initial value 1), D11, D12, . . . D(1)(n−1)}, {(initial value 2), D21, D22, . . . , D(2)(n−1)}, {third group}, . . .

Accordingly, when the actual sensed data is stored as it is, the actual sensed data requires a capacity of "2 bytes×(k−1)". However, when the change amount is stored as described above, the capacity of the change amount may be reduced to a capacity of "1 byte×(k−1)".

Here, the first processor 160 may search for a pattern corresponding to the change amount of the actual sensed data and then may generate alternative sensed data including identification information mapped onto the found pattern instead of storing the actual sensed data.

The bitstream included in a data structure of the alternative sensed data will be described through the second bitstream or the third bitstream.

BITSTREAM2: {(initial value 1), P1, P2, P1}, {(initial value 2), P2, P1, P1}, {third group}, . . .

BITSTREAM3: {(initial value 3), P3, P4, P5}, {(initial value 4), P5, P4, P5}

Accordingly, when the first bitstream BITSTREAM1 is compared with a second bitstream BITSTREAM2 or a third bitstream BITSTREAM3 described above, the size of data may be reduced from "1 byte×(k−1)" to "1 to 2 bytes".

Afterward, the server 30 may find and decode actual sensed data mapped onto an identifier of the alternative sensed data received from the apparatus 10 in the same table stored in the apparatus 10.

Accordingly, the apparatus 10 may reduce the storage capacity of the apparatus 10 by storing the alternative sensed data generated depending on the first storage mode instead of storing all the actual sensed data.

Next, the second storage mode may be a mode in which the actual sensed data is stored depending on the original capacity.

While the first storage mode is activated, when the change amount is greater than the threshold change amount, the first processor 160 may deactivate the first storage mode and may activate the second storage mode.

Moreover, the first processor 160 may store the actual sensed data in a storage method provided by the activated storage mode.

That is, the first processor 160 may store the actual sensed data depending on the original capacity based on the storage method provided by the activated second storage mode.

Here, for example, when the storage mode is changed from the first storage mode to the second storage mode, a fourth bitstream BITSTREAM4 included in a data structure when the actual sensed data is stored is as follows.

BITSTREAM4: {(initial value 5), P3, P4, break}, {(original value 1), (original value 2), (original value 3), . . . }

That is, referring to the fourth bitstream, when an original value is stored in a storage method according to the first storage mode before the fourth pattern P4 and then the change amount of the actual sensed data sensed after the fourth pattern P4 is greater than the threshold change amount, the original value may be stored in the storage method according to the second storage mode.

Afterward, when the predetermined time elapses while the second storage mode is activated, the first processor 160 may calculate a change amount of the actual sensed data sensed at a specific point in time and at the immediately next specific point in time after the predetermined period expires from the specific point in time.

Besides, when the change amount is less than the predetermined threshold change amount, the first processor 160 may deactivate the second storage mode and may activate the first storage mode.

On the other hand, when the change amount is greater than the predetermined threshold change amount, the first processor 160 may maintain the second storage mode during a predetermined time.

Here, the capacity of the first storage mode may be smaller than the capacity of the second storage mode. Afterward, when the first storage mode is activated, the first processor 160 may generate and display a two-dimensional code based on the alternative sensed data.

Here, the two-dimensional code may include a bar code or a QR code.

In detail, the QR code has a two-dimensional configuration capable of recording up to 7,089 numbers, 4,296 characters, and 1,817 Chinese characters by using horizontal and vertical sizes. The QR code may include an Internet address (URL) having a long sentence, photo and video information, map information, business card information, and the like.

In a QR code, as the number of square points increases, more information may be recorded. However, as the number of points increases, the required area may increase. Also, the QR code is superior to a general barcode in recognition speed, recognition rate, and resilience.

Furthermore, because the QR code has a square in shape, the QR code may be accurately recognized even when the QR code is read 360 degrees in any direction. Because the QR code is hardly affected by a background picture, the QR code may be inserted into various types of promotional materials.

The existing one-dimensional barcode may store only numeric information of about 20 numbers. On the other hand, the QR code may store up to 7,089 numeric characters, up to 4,296 characters (ASCII), up to 2,953 bytes for binary (8-bit), and up to 1,817 Chinese characters. The QR code is superior to a general barcode in recognition speed, recognition rate, and resilience.

The barcode is mainly used for calculation, inventory management, and product check. On the other hand, the QR code is widely used as a means of marketing, promotion, and PR means.

Besides, because a dedicated external terminal capable of reading out an existing barcode is owned by only a product seller, it has been impossible for consumers to identify information through the barcode. However, for the QR code, the consumers may directly obtain product information with a smartphone. Users of smartphones download a free QR code scanning application. When the users scan a QR code posted on billboards, promotional papers, posters, magazines, and Internet by using the smartphones, the users may easily obtain various types of information.

For example, a data structure at a point in time when the first processor 160 stores the actual sensed data or the alternative sensed data in a storage method provided in the activated storage mode will be described in detail below with reference to FIG. 9.

Referring to FIG. 9, the data structure may include a header and a body. Bits or bytes having a predetermined size may be allocated to the header and the body.

Here, the header may include a plurality of fields. Identification information indicating a storage mode may be recorded in a first field 901. Identification information indicating the start time and end time at which actual sensed data is sensed may be recorded in a second field 902. Also, identification information indicating a period sensed by the first sensor 200 or the second sensor 120 may be recorded in a third field 903. Moreover, identification information indicating a time interval for calculating a change amount of the actual sensed data may be recorded in a fourth field 904. Also, identification information indicating a location in a body of pattern identification information indicating a pattern may be recorded in a fifth field 905.

Besides, identification information indicating a sign (+ or −) of a change amount of the actual sensed data, identification information indicating the number of decimal places in the actual sensed data, and identification information indicating overflow determination criteria may be recorded in the header.

Such the information recorded in the header may include at least one, and the order may be changed.

Furthermore, at least one of first actual sensed data at a start time at which the actual sensed data is sensed, pattern identification information indicating a pattern, and the actual sensed data may be recorded in the body.

As such, at least one of information recorded in a field of the header may be recorded in the body, and information recorded in the body may be recorded in the header.

Moreover, when 4 bits are assigned to the body, because the most significant bit (MSB) of "1000" is "1", an overflow state may be detected.

The first processor 160 may generate a two-dimensional code based on the actual sensed data or the alternative sensed data and then may display the two-dimensional code on the screen of the first display unit 140. Here, the two-dimensional QR code may be converted and displayed on the screen depending on the order in which the QR codes are generated.

When the first processor 160 is connected to the first sensor 200 through the AUX cable 300, the first processor 160 may activate the first sensor 200 and may deactivate the second sensor 120.

Here, the first sensor 200 and the second sensor 120 may have different sensitivity level ranges from each other.

Accordingly, the first processor 160 may periodically receive a sensed result inside the region 3 from the activated first sensor 200 and then may generate the actual sensed data based on the sensed result received periodically.

Moreover, when the first processor 160 is paired with the external terminal 20 through the short-range communication unit 111, the first processor 160 may transmit the actual sensed data or the alternative sensed data, which is based on the sensed result of the activated one of the first sensor 200 and the second sensor 120, to the external terminal 20 in real time through short-distance communication.

When the external terminal 20 is paired, the first processor 160 may transmit the actual sensed data or the alternative sensed data to the external terminal 20 in real time. The first processor 160 may stop generating the two-dimensional code for the actual sensed data or the alternative sensed data.

Here, when pairing with the external terminal 20 is unpaired, the first processor 160 may resume the generating of the two-dimensional code on the first display unit 140.

Also, while the generating of the two-dimensional code is stopped, the first processor 160 may turn off the screen of the first display unit 140. Alternatively, while the generating of the two-dimensional code is stopped, the first processor 160 may display the two-dimensional code displayed at a point in time when the generating of the two-dimensional code is stopped.

Moreover, the first processor 160 may display a two-dimensional code indicating address information of a website providing a logistics state management service on the first display unit 140.

Here, the two-dimensional code indicating address information may be fixedly displayed on the first display unit 140.

Alternatively, the two-dimensional code indicating address information may be attached in a form of a sticker to the outside of the region 3 where the logistics of the delivery vehicle 2 is loaded.

Next, the external terminal 20 will be described based on FIG. 4.

The external terminal 20 may be an electronic device capable of recognizing a two-dimensional code possessed by a delivery person who delivers logistics, a person in charge of managing logistics, or the like. Here, the external terminal 20 may include all kinds of handheld-based wireless communication devices, which are capable of being connected to a web server through a network, such as a mobile phone, a smartphone, a personal digital assistant (PDA), a portable multimedia player (PMP), a tablet PC, or the like.

The external terminal 20 may include a second communication unit 210, a second input unit 220, a second display unit 230, a second memory 240, and a second processor 250. Herein, the external terminal 20 may include fewer or more components than the components illustrated in FIG. 4.

The second communication unit 210 may include one or more modules that enable wireless communication between the external terminal 20 and a wireless communication system, between the external terminal 20 and the apparatus 10, between the external terminal 20 and the server 30, or between the external terminal 20 and an external server (not illustrated). Furthermore, the second communication unit 210 may include one or more modules connecting the external terminal 20 to one or more networks.

Moreover, the second communication unit 210 may further include a short-range communication unit 211 that performs low-power Bluetooth (Bluetooth™ Low Energy) communication with the apparatus 10.

The second input unit 220 may be used to enter image information (or signal), audio information (or signal), data, or information entered by a user. To enter image information, the external terminal 20 may include at least one camera on a front surface or a rear surface thereof.

Here, the camera may process an image frame such as a still image or a moving image, which is obtained by an image sensor in a video call mode or a shooting mode. The processed image frame may be displayed on the second display unit 230 or may be stored in the second memory 240.

In the meantime, the at least one camera provided in the external terminal 20 may be positioned to have a matrix structure. Pieces of image information having various angles or focal points may be entered into the external terminal 20 through the camera having the matrix structure in this manner.

Furthermore, the camera may be positioned in a stereo structure to obtain a left image and a right image for implementing a stereoscopic image.

Moreover, the camera may capture an image or video depending on a user's operation. Here, the camera may be a recognizer capable of capturing a QR code provided by the apparatus 10 depending on the user's operation.

The second input unit 220 may be used to receive information from the user. When the information is entered through the second input unit 220, the second processor 250 may control the operation of the external terminal 20 to correspond to the entered information.

The second input unit 220 may include a mechanical input means (or a mechanical key, for example, a button positioned on the front, rear, or side of the external terminal 20, a dome switch, a jog wheel, a jog switch, or the like) and a touch input means. For example, the touch input means may consist of a virtual key, a soft key, or a visual key displayed on a touch screen through software processing or may consist of a touch key positioned on a portion other than the touch screen. In the meantime, the virtual key or the visual key may be displayed on the touch screen while having various shapes. For example, the virtual key or visual key may be formed of graphics, texts, icons, video, or a combination thereof.

The second display unit 230 may have a mutual layer structure with the touch sensor or may be integrated with the touch sensor. Accordingly, the second display unit 230 may implement the touch screen. Such the touch screen may provide an input interface between the external terminal 20 and a user and may, at the same time, provide an output interface between the external terminal 20 and the user.

When the camera of the second input unit 220 recognizes a two-dimensional code provided by the apparatus 10, the second display unit 230 may display the recognized two-dimensional code and actual sensed data included in the recognized two-dimensional code.

The second memory 240 may store data for supporting various functions of the external terminal 20. The second memory 240 may store a plurality of application programs (or applications) running in the external terminal 20, data for an operation of the external terminal 20, and instructions. At least part of the application programs may be downloaded from an external server (not illustrated) through wireless communication. Moreover, at least part of these applications may be present for basic functions (e.g., an incoming and outgoing call function or an incoming and outgoing message function) of the external terminal 20. In the meantime, the application program may be stored in the second memory 240, may be installed in the external terminal 20, and may be driven by the second processor 250 so as to perform an operation (or function) of the external terminal 20.

In addition to an operation associated with the application program, the second processor 250 may generally control overall operations of the external terminal 20. The second processor 250 may provide or process appropriate information or functions to a user, by processing a signal, data, information, or the like, which is input or output through the above-described components, or driving the application program stored in the second memory 240.

Besides, the second processor 250 may control at least part of the components described with reference to FIG. 4 to operate the application program stored in the second memory 240. Furthermore, the second processor 250 may combine and operate at least two or more of the components included in the external terminal 20 to operate the application program.

The second processor 250 may transmit the two-dimensional code captured through the camera to the server 30.

That is, when the second processor 250 captures the two-dimensional code displayed on the apparatus 10 through the camera, the second processor 250 may transmit the two-dimensional code to the server 30.

Next, the server 30 will be described based on FIG. 5.

The server 30 may recognize the two-dimensional code in the captured image received from the external terminal 20 and then may recognize identification information in the recognized two-dimensional code.

Moreover, the server 30 may identify the recognized identification information among pre-stored pieces of identification information and then may search for the actual sensed data associated with the identified identification information.

Afterward, the server 30 may manage the state of the logistics based on the found result.

The server 30 may include all kinds of handheld-based wireless communication devices, which are capable of being connected to a web server through a network, such as a mobile phone, a smartphone, a personal digital assistant (PDA), a portable multimedia player (PMP), a tablet PC, or the like. In addition, the external device 30 may be one of digital devices, which are equipped with a memory means and which have computing power by mounting a microprocessor, such as a personal computer (e.g., a desktop computer, a notebook computer, or the like), a workstation, a PDA, a web pad, or the like.

The server 30 may include a third communication unit 310, a third memory 320, and a third processor 330. Herein, the server 30 may include fewer or more components than the components illustrated in FIG. 5.

The third communication unit 310 may include one or more modules that enable wireless communication between the server 30 and a wireless communication system, between the server 30 and the apparatus 10, between the server 30 and the external terminal 20, or between the server 30 and an external server (not illustrated). Furthermore, third communication unit 310 may include one or more modules connecting the server 30 to one or more networks.

The third memory 320 may store a plurality of application programs (or applications) running in the server 30, data for an operation of the server 30, and instructions. At least part of the application programs may be downloaded from an external server (not illustrated) through wireless communication. Besides, at least part of the application programs may be present for basic functions of the server 30. In the meantime, the application program may be stored in the third memory 320, may be installed in the server 30, and may be driven by the third processor 330 so as to perform an operation (or function) of the server 30.

Here, the third memory 320 may further include a database 321. The database 321 may store pieces of actual sensed data for respective identification information. That is, the database 321 may store a table in which the corresponding identification information about a pattern indicating each of the plurality of change amounts is mapped onto the corresponding actual sensed data.

In addition to an operation associated with the application program, the third processor 330 may generally control overall operations of the server 30. The third processor 330 may provide or process appropriate information or functions to a user, by processing a signal, data, information, or the like, which is input or output through the above-described components, or driving the application program stored in the third memory 330.

Besides, the third processor 330 may control at least part of the components described with reference to FIG. 5 to operate the application program stored in the third memory 320. Furthermore, the third processor 330 may combine and operate at least two or more of the components included in the server 30 to operate the application program.

The third processor 330 may recognize the two-dimensional code in the captured image received from the external terminal 20 and then may recognize identification information in the recognized two-dimensional code.

Here, the two-dimensional code may be generated based on the alternative sensed data generated while the first storage mode is activated.

The third processor 330 may identify the recognized identification information among pieces of identification information stored in the database 321 and then may search for the actual sensed data associated with the identified identification information.

In detail, the third processor 330 may search for the actual sensed data associated with the grasped identification information in a table, which is stored in the database 321 and which is the same as a table stored in the external terminal 20.

Afterward, the third processor 330 may manage the state of the logistics through the actual sensed data based on the found result.

That is, when it is determined, based on the actual sensed data of the logistics identified based on the found result, that the actual sensed data is out of a predetermined threshold range, the third processor 330 may generate a warning signal and may transmit the warning signal to the external terminal 20.

When the two-dimensional code captured through the camera is received from the external terminal 20, the third processor 330 may grasp actual sensed data included in a two-dimensional code, may generate a new two-dimensional code based on status information and time information at a point in time when the two-dimensional code is received, and may transmit the new two-dimensional code to the external terminal 20.

That is, the third processor 330 may generate the new two-dimensional code by excluding the actual sensed data sensed before that based on the time information, and then may transmit the new two-dimensional code to the external terminal 20.

Next, the external server (not illustrated) may refer to a device, which needs to receive status information in the delivery vehicle, such as a server that collectively manages logistics, a server of a producer that delivers the logistics, and a server of a customer that receives the logistics.

Alternatively, the external server (not illustrated) may be a device that provides a download of an application for providing a logistics state management service.

Here, the external server may include all kinds of handheld-based wireless communication devices, which are capable of being connected to a web server through a network, such as a mobile phone, a smartphone, a personal digital assistant (PDA), a portable multimedia player (PMP), a tablet PC, or the like. In addition, the external device 30 may be one of digital devices, which are equipped with a memory means and which have computing power by mounting a microprocessor, such as a personal computer (e.g., a desktop computer, a notebook computer, or the like), a workstation, a PDA, a web pad, or the like.

Next, the communication network 40 may transmit or receive various pieces of information between the apparatus 10, the external terminal 20, the server 30, and the external server (not illustrated). Various types of communication networks may be used. For example, wireless communication methods such as wireless LAN (WLAN), Wi-Fi, Wibro, Wimax, High Speed Downlink Packet Access (HSDPA), and the like or wired communication methods such as Ethernet, xDSL (ADSL or VDSL), Hybrid Fiber Coax (HFC), Fiber to The Curb (FTTC), Fiber to The Home (FTTH), and the like may be used in the communication network 40.

In the meantime, the communication network 40 is not limited to the communication method described above, and may include all types of communication methods widely known or to be developed in the future in addition to the above communication methods.

Figure 10:
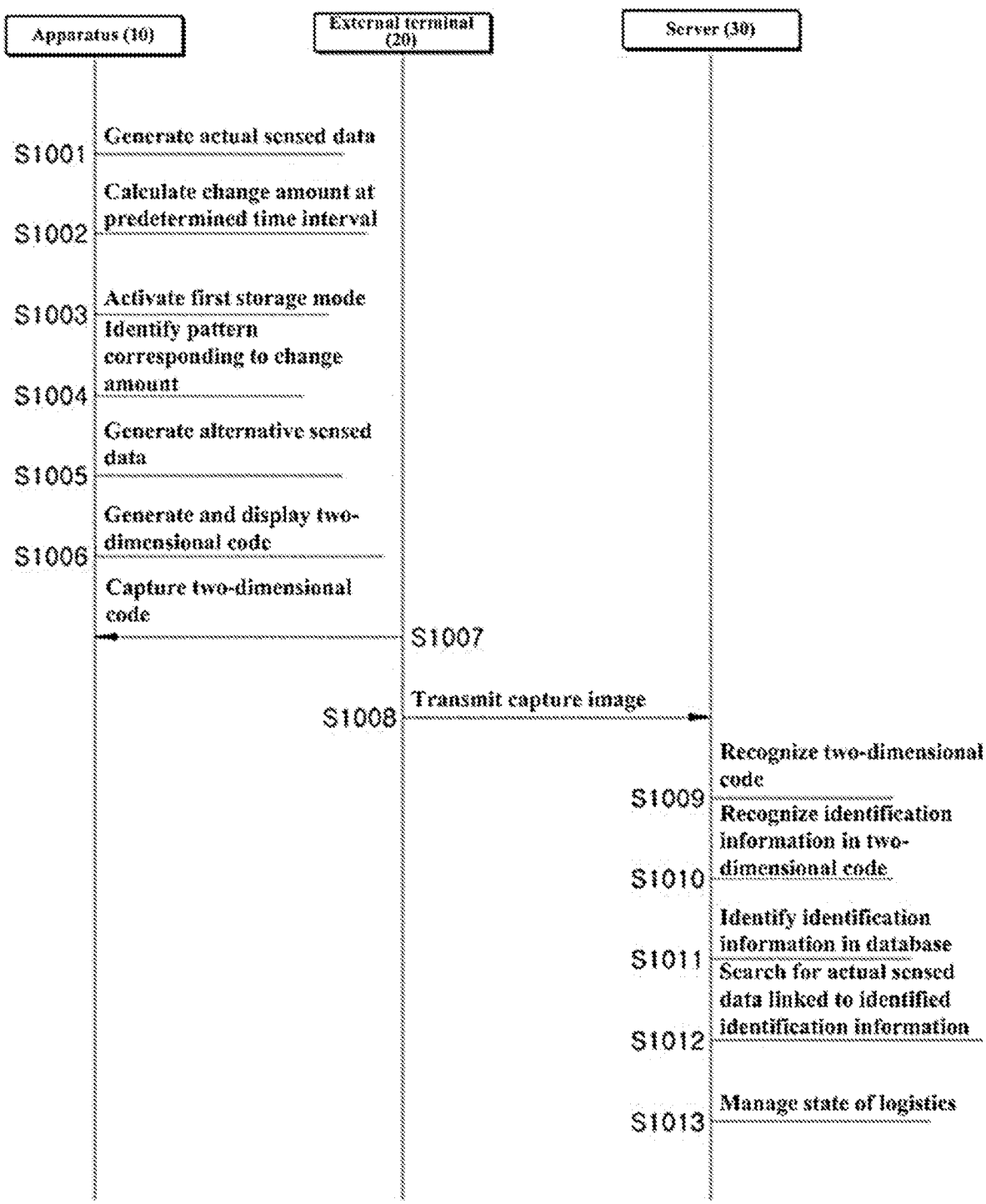
FIG. 10 is a flowchart illustrating an operation of one embodiment of a system for compressing and storing data based on the amount of change in sensed data used for state management of a logistics, according to an embodiment of the inventive concept.

FIG. 10 is a flowchart illustrating an operation of one embodiment of the system 1 for compressing and storing data based on the amount of change in sensed data used for state management of a logistics, according to an embodiment of the inventive concept.

The apparatus 10 may generate actual sensed data, which is obtained by sensing an internal state of the region 3 at a predetermined period through the first sensor 200 installed in the region 3 where a logistics is loaded (S1001).

In detail, the apparatus 10 may generate actual sensed data obtained by periodically sensing at least one of the temperature, acceleration, humidity, illuminance, inclination, impact, and location inside a region through the first sensor 200 installed in the region 3 where the logistics of the delivery vehicle 2 is loaded.

The apparatus 10 may calculate a change amount of the actual sensed data at a predetermined time interval (S1002).

When the change amount is smaller than the threshold change amount, the apparatus 10 may activate the first storage mode depending on a result of comparison between the change amount and the predetermined threshold change amount (S1003).

In the meantime, when the change amount is greater than the threshold change amount, the apparatus 10 may activate the second storage mode depending on the result of comparison between the change amount and the predetermined threshold change amount.

When the first storage mode is activated, the apparatus 10 may identify a pattern, which corresponds to the change amount, from among a plurality of patterns for each change amount (S1004).

The apparatus 10 may identify identification information corresponding to the identified pattern among the pieces of identification information and then may generate the alternative sensed data including the identified identification information (S1005).

Here, the apparatus 10 may store the alternative sensed data instead of the actual sensed data.

The apparatus 10 may generate and display a two-dimensional code based on the alternative sensed data (S1006).

The external terminal 20 may capture the two-dimensional code through the camera (S1007) and then may transmit a capture image to the server 30 (S1008).

The server 30 may recognize the two-dimensional code in the capture image received from the external terminal 20 (S1009).

The server 30 may recognize identification information in the recognized two-dimensional code (S1010) and then may identify the recognized identification information among the pieces of identification information stored in the database (S1011).

The server 30 may search for the actual sensed data linked to the identified identification information (S1012) and then may manage the state of the logistics based on the found result (S1013).

FIG. 10 illustrates that step S1001 to step S1013 are performed sequentially. However, this is merely illustrative of the technical idea of the inventive concept. Those skilled in the art to which an embodiment of the inventive concept belongs may apply various modifications and variations by changing and performing the order illustrated in FIG. 10 or performing one or more of step S1001 to step S1013 in parallel without departing from the essential characteristics of an embodiment of the inventive concept. The embodiment in FIG. 10 is not limited to a time-series order.

Figure 11:
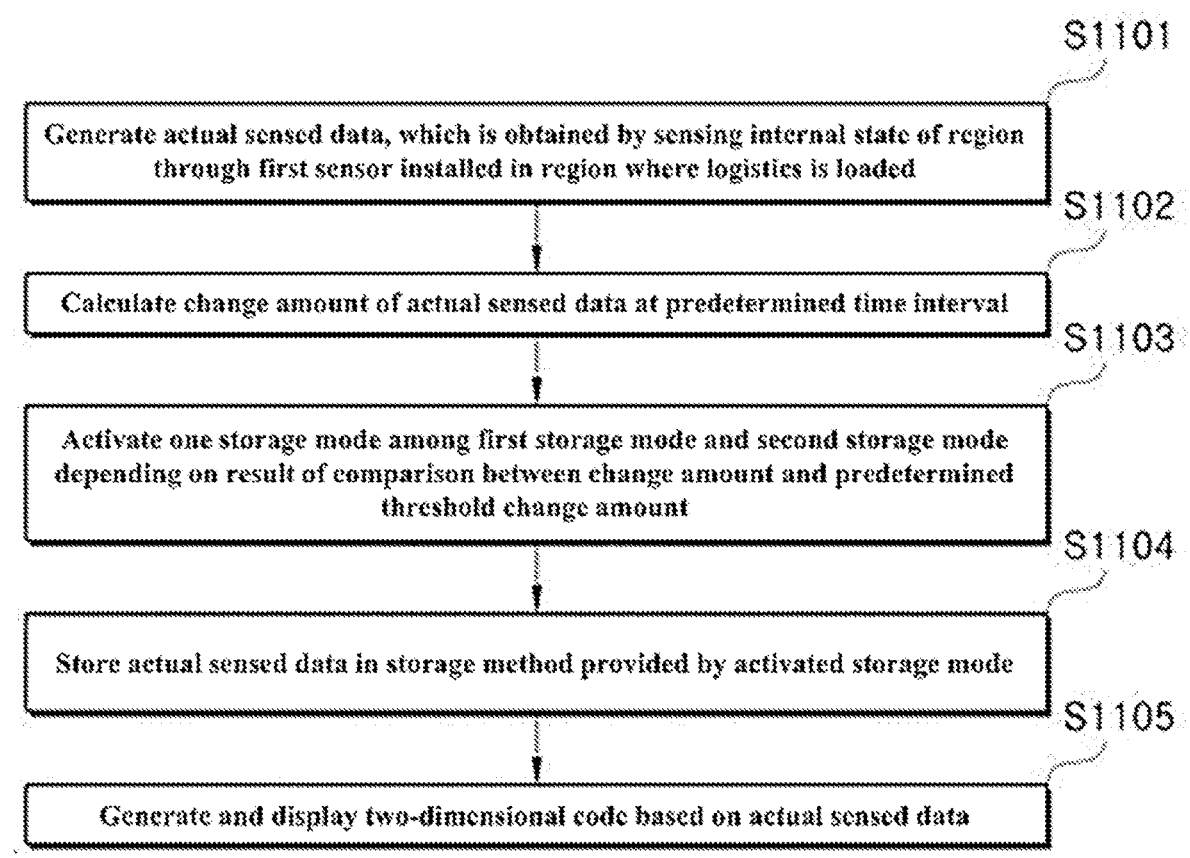
FIG. 11 is a flowchart illustrating an operation of a first processor for compressing and storing data based on the amount of change in sensed data used for state management of a logistics, according to an embodiment of the inventive concept.

FIG. 11 is a flowchart illustrating an operation of the first processor 160 for compressing and storing data based on the amount of change in sensed data used for state management of a logistics, according to an embodiment of the inventive concept. Hereinafter, an operation of the first processor 160 may be performed by the apparatus 10.

The first processor 160 may generate actual sensed data, which is obtained by sensing an internal state of the region 3 through the first sensor 200 installed in the region 3 where a logistics is loaded (S1101).

In detail, the first processor 160 may generate the actual sensed data obtained by periodically sensing at least one of a temperature, acceleration, humidity, illuminance, inclination, impact and location inside the region through the first sensor installed in the region where the logistics of the delivery vehicle is loaded.

The first processor 160 may calculate a change amount of the actual sensed data at a predetermined time interval (S1102).

The first processor 160 may activate one storage mode among the first storage mode and the second storage mode depending on a result of comparison between the change amount and a predetermined threshold change amount (S1103).

In detail, when the change amount is less than the threshold change amount, the first processor 160 may activate the first storage mode.

Here, the first storage mode may be a mode in which the actual sensed data is replaced with alternative sensed data including a pattern indicated by the change amount and then stored. Such the alternative sensed data may have a smaller capacity than the actual sensed data and may further include a time at which the actual sensed data is sensed.

On the other hand, when the change amount is greater than the threshold change amount, the first processor 160 may activate the second storage mode.

Here, the second storage mode may be a mode in which the actual sensed data is stored depending on the original capacity.

The first processor 160 may store the actual sensed data in a storage method provided by the activated storage mode (S1104).

Here, when the first storage mode is activated, the first processor 160 may identify a pattern corresponding to the change amount among a plurality of patterns for each change amount and then may identify identification information corresponding to the identified pattern among the pieces of identification information.

Moreover, the first processor 160 may generate the alternative sensed data including the identified identification information and then may store the alternative sensed data instead of the actual sensed data.

At this time, the alternative sensed data may be smaller in capacity than the actual sensed data. That is, the alternative sensed data may be generated by identifying the pattern of the actual sensed data instead of the actual sensed data and including only identification information indicating the pattern, and may have a smaller capacity than the actual sensed data.

The first processor 160 may generate and display a two-dimensional code based on the actual sensed data (S1105).

FIG. 11 illustrates that step S1101 to step S1105 are performed sequentially. However, this is merely illustrative of the technical idea of the inventive concept. Those skilled in the art to which an embodiment of the inventive concept belongs may apply various modifications and variations by changing and performing the order illustrated in FIG. 11 or performing one or more of step S1101 to step S1105 in parallel without departing from the essential characteristics of an embodiment of the inventive concept. The embodiment in FIG. 11 is not limited to a time-series order.

The method according to an embodiment of the inventive concept may be implemented by a program (or an application) and may be stored in a medium such that the program is executed in combination with a server being hardware.

The above-described program may include a code encoded by using a computer language such as C, C++, JAVA, a machine language, or the like, which a processor (CPU) of the computer may read through the device interface of the computer, such that the computer reads the program and performs the methods implemented with the program. The code may include a functional code related to a function that defines necessary functions executing the method, and the functions may include an execution procedure related control code necessary for the processor of the computer to execute the functions in its procedures. Furthermore, the code may further include a memory reference related code on which location (address) of an internal or external memory of the computer should be referenced by the media or additional information necessary for the processor of the computer to execute the functions. Further, when the processor of the computer is required to perform communication with another computer or a server in a remote site to allow the processor of the computer to execute the functions, the code may further include a communication related code on how the processor of the computer executes communication with another computer or the server or which information or medium should be transmitted/received during communication by using a communication module of the computer.

The steps of a method or algorithm described in connection with the embodiments of the inventive concept may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form known in the art to which the inventive concept pertains.

Although embodiments of the inventive concept have been described herein with reference to accompanying drawings, it should be understood by those skilled in the art that the inventive concept may be embodied in other specific forms without departing from the spirit or essential features thereof. Therefore, the above-described embodiments are exemplary in all aspects, and should be construed not to be restrictive.

According to an embodiment of the inventive concept, it is possible to store and manage the capacity of data indicating status information of a logistics by providing a method for storing status information of logistics, which is obtained by sensing at least one of the temperature, acceleration, humidity, illuminance, inclination, impact, and location of the inside of a delivery vehicle that delivers the logistics, in a predetermined storage method.

Moreover, according to an embodiment of the inventive concept, a lot of data may be included in one page by compressing the status information stored in a form of a QR code, thereby increasing the efficiency of logistics-related task.

Effects of the inventive concept are not limited to the effects mentioned above, and other effects not mentioned will be clearly understood by those skilled in the art from the following description.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A storage method of sensed data used for state management of a logistics, which is performed by an apparatus, the method comprising:
generating actual sensed data, which is obtained by sensing at least one of a temperature, acceleration, humidity, illuminance, inclination, impact, and location inside a region at a predetermined period through a first sensor installed inside the region where the logistics of a delivery vehicle is loaded;
calculating a change amount of the actual sensed data at a predetermined time interval;
activating one storage mode among a first storage mode and a second storage mode depending on a result of comparison between the change amount and a predetermined threshold change amount; and
storing the actual sensed data in a storage method provided in the activated storage mode,
wherein the activating includes:
when the change amount is smaller than the threshold change amount, activating the first storage mode,
wherein the first storage mode is a mode in which the actual sensed data is replaced with alternative sensed data including a pattern indicated by the change amount and is stored,
wherein the alternative sensed data is smaller in capacity than the actual sensed data, and
wherein the second storage mode is a mode in which the actual sensed data is stored depending on an original capacity.

2. The method of claim 1, wherein the activating includes:
while the first storage mode is activated, when the change amount is greater than the threshold change amount, deactivating the first storage mode and activating the second storage mode.

3. The method of claim 1, further comprising:
storing, by the apparatus, pieces of identification information indicating change amounts of a plurality of patterns;
when the first storage mode is activated, identifying, by the apparatus, the pattern, which corresponds to the change amount, from among the plurality of patterns;
identifying, by the apparatus, identification information corresponding to the identified pattern from among the pieces of identification information;
generating, by the apparatus, the alternative sensed data including the identified identification information; and
storing, by the apparatus, the alternative sensed data instead of the actual sensed data.

4. The method of claim 3, wherein the alternative sensed data further includes a time at which the actual sensed data is sensed.

5. The method of claim 3, further comprising:
generating and displaying a two-dimensional code based on the alternative sensed data,
wherein the two-dimensional code is captured by an external terminal and is transmitted to a server.

6. The method of claim 5, wherein pieces of actual sensed data for each of the pieces of identification information are stored in a database of the server,
further comprising:
recognizing, by the server, the two-dimensional code within a capture image received from the terminal;
recognizing, by the server, identification information within the recognized two-dimensional code;
identifying, by the server, the recognized identification information among the pieces of identification information stored in the database;
searching, by the server, for actual sensed data linked to the identified identification information; and
managing, by the server, a state of the logistics based on a result of the searching.

7. A storage apparatus of sensed data used for state management of a logistics, the storage apparatus comprising:
a first sensor installed inside a region where the logistics of a delivery vehicle is loaded and configured to sense at least one of a temperature, acceleration, humidity, illuminance, inclination, impact, and location inside a region at a predetermined period; and
a processor,
wherein the processor is configured to:
generate actual sensed data depending on a results of sensing of the first sensor;
calculate a change amount of the actual sensed data at a predetermined time interval;
activate one storage mode among a first storage mode and a second storage mode depending on a result of comparison between the change amount and a predetermined threshold change amount; and
store the actual sensed data in a storage method provided in the activated storage mode,
wherein, during the activation, the processor is configured to:
when the change amount is smaller than the threshold change amount, activate the first storage mode,
wherein the first storage mode is a mode in which the actual sensed data is replaced with alternative sensed data including a pattern indicated by the change amount and is stored,
wherein the alternative sensed data is smaller in capacity than the actual sensed data, and
wherein the second storage mode is a mode in which the actual sensed data is stored depending on an original capacity.

8. The storage apparatus of claim 7, wherein during the activation, the processor is configured to:
while the first storage mode is activated, when the change amount is greater than the threshold change amount, deactivate the first storage mode and activate the second storage mode.

9. The storage apparatus of claim 7, wherein the processor is configured to:
store pieces of identification information indicating change amounts of a plurality of patterns;
when the first storage mode is activated, identify the pattern, which corresponds to the change amount, from among the plurality of patterns;
identify identification information corresponding to the identified pattern from among the pieces of identification information;
generate the alternative sensed data including the identified identification information; and
store the alternative sensed data instead of the actual sensed data.

10. The storage apparatus of claim 9, wherein the alternative sensed data further includes a time at which the actual sensed data is sensed.

11. The storage apparatus of claim 9, wherein the processor is configured to:

generate and display a two-dimensional code based on the alternative sensed data, and wherein the two-dimensional code is captured by an external terminal and is transmitted to a server.

12. The storage apparatus of claim 11, wherein pieces of actual sensed data for each of the pieces of identification information are stored in a database of the server, and wherein the server is configured to:

recognize the two-dimensional code within a capture image received from the terminal;

recognize identification information within the recognized two-dimensional code;

identify the recognized identification information among the pieces of identification information stored in the database;

search for actual sensed data linked to the identified identification information; and manage a state of the logistics based on a result of the searching.

13. A non-transitory computer-readable recording medium storing a computer program, and configured to be coupled to a computer hardware including a processor, the program includes instructions to execute a method for storing sensed data used for state management of a logistics, wherein the computer program, when executed, causes the processor to:

generate actual sensed data, which is obtained by sensing at least one of a temperature, acceleration, humidity, illuminance, inclination, impact, and location inside a region at a predetermined period through a first sensor installed inside the region where the logistics of a delivery vehicle is loaded;

calculate a change amount of the actual sensed data at a predetermined time interval;

activate one storage mode among a first storage mode and a second storage mode depending on a result of comparison between the change amount and a predetermined threshold change amount; and store the actual sensed data in a storage method provided in the activated storage mode, wherein, during the activation, the computer program causes the processor to:

when the change amount is smaller than the threshold change amount, activate the first storage mode, wherein the first storage mode is a mode in which the actual sensed data is replaced with alternative sensed data including a pattern indicated by the change amount and is stored, wherein the alternative sensed data is smaller in capacity than the actual sensed data, and wherein the second storage mode is a mode in which the actual sensed data is stored depending on an original capacity.

* * * * *